US00PP34075P3

(12) United States Plant Patent
Drury

(10) Patent No.: US PP34,075 P3
(45) Date of Patent: Mar. 29, 2022

(54) HOP PLANT NAMED 'CV12'

(50) Latin Name: *Humulus lupulus*
Varietal Denomination: CV12

(71) Applicant: CV Hops LLC, Bloomington, IN (US)

(72) Inventor: Douglas W. Drury, Bloomington, IN (US)

( * ) Notice: Subject to any disclaimer, the term of this patent is extended or adjusted under 35 U.S.C. 154(b) by 0 days.

(21) Appl. No.: 16/873,817

(22) Filed: Jul. 14, 2020

(65) Prior Publication Data

US 2022/0022354 P1 Jan. 20, 2022

(51) Int. Cl.
*A01H 5/08* (2018.01)
*A01H 6/28* (2018.01)

(52) U.S. Cl.
USPC ..... Plt./236
CPC ..... *A01H 6/28* (2018.05)

(58) Field of Classification Search
USPC ..... Plt./236
CPC ..... A01H 6/28
See application file for complete search history.

(56) References Cited

U.S. PATENT DOCUMENTS

PP14,127 P2 * 9/2003 Gamache et al. ..... A01H 6/28 Plt./236
PP15,663 P2 * 3/2005 Zimmermann ..... A01H 6/28 Plt./236
2019/0289804 A1 * 9/2019 Boudko et al. ..... A01H 1/06

OTHER PUBLICATIONS

"Artificially induced polyploidization in *Humulus lupulus* L. and its effect on morphological and chemical traits", Anna Trojak-Goluch and Urszula Skomra, Breeding Science 63: 393-399 (2013).*
"DNA Content of Colchicine-induced Endopolyploid Nuclei in Vicia Faba L.", M.D. Bennett adn A.J. Jellings, Heredity (1975), 35, (2), 261-272.*

* cited by examiner

*Primary Examiner* — Anne Marie Grunberg
(74) *Attorney, Agent, or Firm* — Maginot, Moore & Beck, LLP

(57) ABSTRACT

A new hop plant named 'CV12' is disclosed. 'CV12' is notable for its increased cone size, relatively high myrcene content and unique spicey, piney, citrus aroma profile.

5 Drawing Sheets

Genus and species: *Humulus lupulus*.
Variety denomination: CV12.

STATEMENT REGARDING FEDERALLY SPONSORED RESEARCH OR DEVELOPMENT

None.

BACKGROUND

*Humulus lupulus*, also referred to as hop or common hop, is a flowering plant in the Cannabaceae family, native to Europe, western Asia and North America. It is an herbaceous, perennial that dies back, overwinters as a rhizome, and sends up new shoots in early spring. The new growth forms climbing bines that are able to reach heights over 20 feet.

Hops are native to the northern hemisphere, and can be found wild in certain parts of North America. Commercial hops are cultivated between the 30th and 50th parallel of both north and south latitudes as well as at varying altitudes. The photoperiodism of hops places its optimal cultivation in these latitudinal bands. Hops is adapted to the utilization of long summer days.

*Humulus Lupulus* is a dioecious species, meaning female and male reproductive organs occur on separate plants. The flowers (cones) of the female hop plant are used in the making of beverage, especially beer, as a flavoring and processing component. It contributes to the bitterness and aroma in beer as well as foam quality, flavor, and taste stability. Male hop plants have no commercial value other than for use in breeding programs. Male hops are kept well away from farms, as pollination and subsequent seed production alters the properties, especially aroma, of the cone.

SUMMARY OF THE INVENTION

The new cultivar of hop, *Humulus lupulus* (common hop or hop), was discovered and selected by the inventor at our laboratory. During the creation of the new variety of the present invention, a specific plant from our farm cultivated for over 80 years (a non-patented, proprietary Hop plant owned by the assignee; hereafter referred to as CVC) was exposed to colchicine during propagation.

More specifically, actively growing shoots were directly treated by infusion with 0.5% (w/v) colchicine solution. Infusion of shoot cells with colchicine occurred by immersing the material in an open container containing the colchicine solution. The submerged shoots as well as the entire parent plant were placed in a 5-gallon vacuum chamber. A vacuum was pulled using a 1 stage, 3 CRM vacuum pump until the pressure inside the chamber reached between −20.00 in·Hg and −29.20 in·Hg relative to atmosphere. To avoid shock during the creation of the vacuum, plants were allowed to gradually acclimate for 15 min as pressure decreased. Once the target pressure was achieved, the pressure was held for 20 min to facilitate the colchicine solution entering the cells. Then, to prevent shock from rapid depressurization, plants were allowed to gradually re-pressurize over the course of 15 minutes. The shoots were rinsed following treatment. Treated plants were placed in 2 gallon pots containing a mixture of potting soil and perlite (3:1). All plants were grown under natural photoperiod in growth chambers.

A number of differing plants were produced by the method. The plant of the present invention, hereafter referred to as CV12, was discovered among the resulting plants. It was found to be different from its starting material in a number of important respects. More specifically, this new plant possessed the following combination of characteristics:

a) Has an increased genome size relative to its parent plant.
b) Has female reproductive organs significantly larger, in length and weight, than those of its parent plant
c) Has an essential oil profile substantially different from its parent plant.

Genome Size:

Cuttings from CV12 plants were taken from plants in the field and propagated in the laboratory. Young leaves from these plants were removed and cells lysed and the DNA content of separated nuclei were measured using a BD Accuri™ C6 Cytometer. 5000 nuclei were tested per plant. CV12 contained a 29% increased per nucleus DNA content relative to CVC. The genomic change of CVC to CV12 is substantial and persists through subsequent propagation.

Cones Significantly Larger:

On average, cones of CV12 are larger than cones of CVC. The average weight of CVC cone is 1.26 g (∓0.07 s.e.) while the CV12 cone average is 1.72 g (∓0.10 SE). This 460 mg difference in mass is significant (one-sided Student's t-test: df=82, t-value=−3.8064, p-value=0.0001347) and results in a 36% increase in mass from CVC to CV12. This increase in the size of female reproductive organs is also seen in the average length of cones. CVC plants average a length of 38.17 mm (∓1.4 SE) while CV12 plants produce cones averaging 43.40 mm (∓1.66 s.e.). This is a significant increase in cone length from CVC to CV12 (one-sided Student's t-test: t-value=2.1528, df=15, p-value=0.02401).

Essential Oil Profile:

CV12 has a substantially increased myrcene content compared to CVC with approximately 57% of oil content of CV12 made up of mycene while CVC has less than 20% myrcene. This change in oil content manifests in a difference in aroma profile between the 2 plant types. CV12 is described as having a Spicey/Piney/Citrus aroma whereas CVC is Spicey/Grassy/Floral.

The new variety of the present invention has been asexually propagated at our farm by softwood cuttings and by rhizome propagation through successive generations, beginning in March, 2019. Such asexual propagation has demonstrated that the unique combination of characteristics has been well established and is transmitted to succesive generations.

COMPARISON TO KNOWN VARIETIES

| Component | CV12 | CVC | Cascade | Centen-nial | Fuggle |
|---|---|---|---|---|---|
| Alpha (as % of cone weight) | 6.40 | 6.9 | 7.40 | 10.20 | 4.40 |
| Beta (as % of cone weight) | 4.90 | 4.8 | 7.00 | 4.00 | 2.70 |
| B-Pinene (as % of total oils) | 1.25 | <0.05 | 0.83 | 1.09 | 0.35 |
| Myrcene (as % of total oils) | 57.66 | 1.05 | 56.33 | 65.37 | 24.24 |
| Linalool (as % of total oils) | 0.37 | <0.04 | 0.49 | 0.67 | 0.78 |

-continued

| Component | CV12 | CVC | Cascade | Centen-nial | Fuggle |
|---|---|---|---|---|---|
| Caryophyllene (as % of total oils) | 5.61 | 14.6 | 6.23 | 5.23 | 14.01 |
| Farnesene (as % of total oils) | <0.05 | <0.05 | 6.30 | 0.20 | 6.54 |
| Humulene (as % of total oils) | 9.89 | 29.35 | 14.19 | 10.68 | 36.37 |
| Geraniol (as % of total oils) | 0.47 | <0.05 | 0.18 | 1.14 | 0.11 |

Known Varieties data from 2021 © Yakima Chief Hops Inc.

BRIEF DESCRIPTION OF THE FIGURES

FIG. 3 shows a cytomoter profile of the CV12 Hop plant, and particularly genome size comparisons or propidium iodide muclei isolated from young leaves of hop CVC plants (black) and hop CV12 plants (grey), where FIG. 3A relates to CV12 leaves taken from clonal generation 3 and FIG. 3B relates to CV12 leaves taken from clonal generation 4.

DETAILED BOTANICAL DESCRIPTION

Figure 1:
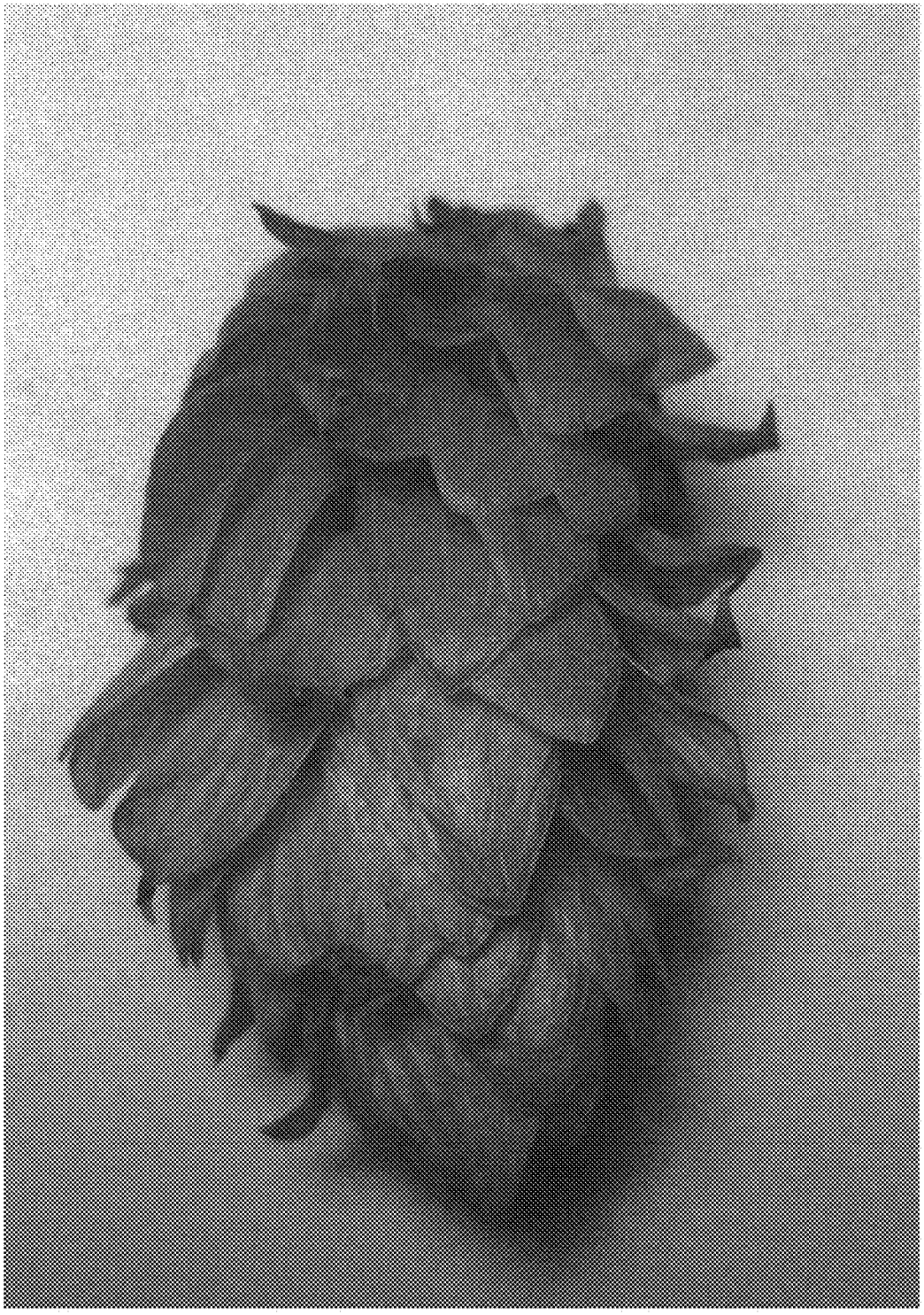
FIG. 1 shows a cone of the CV12 Hop plant.
Figure 2:
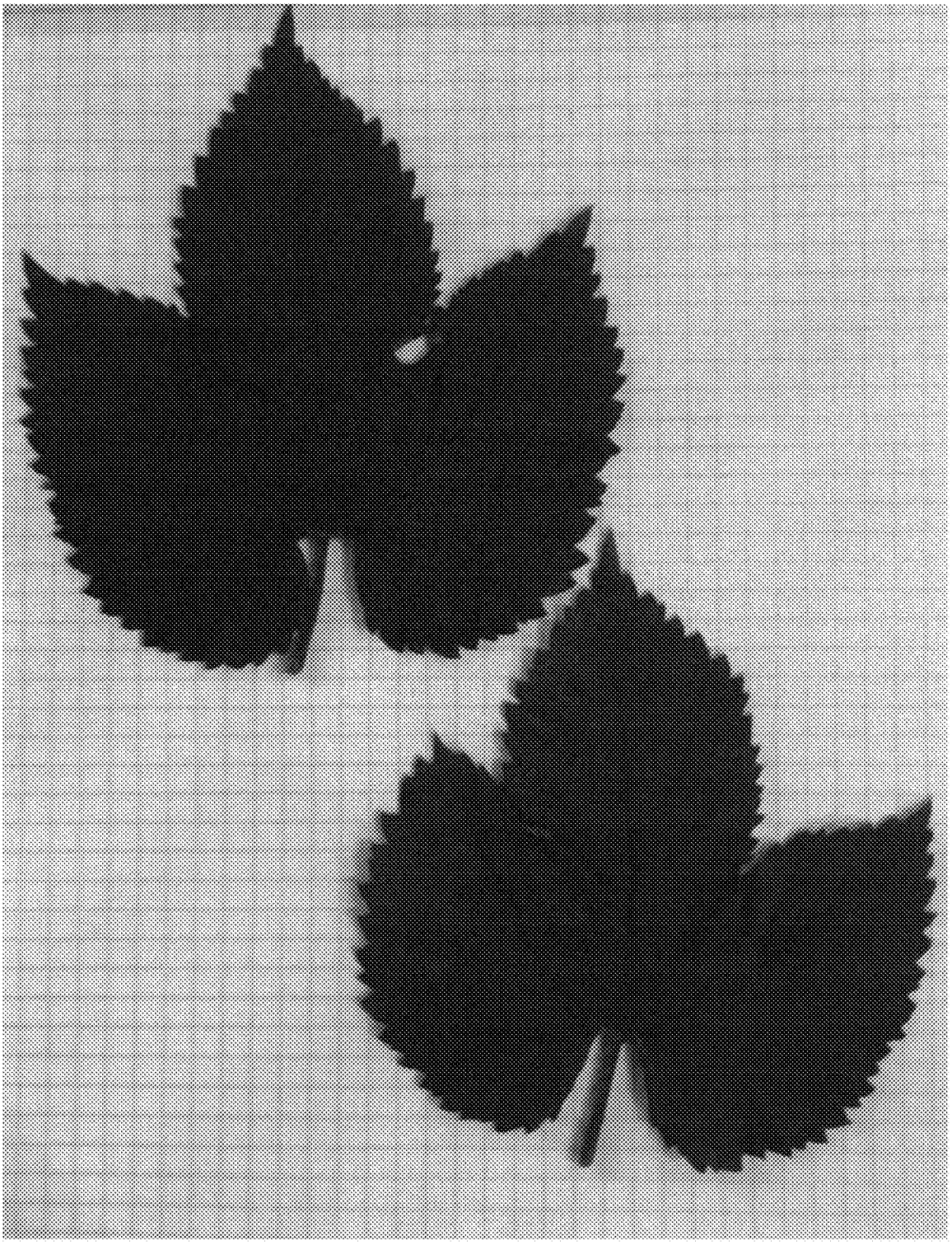
FIG. 2 shows leaves of the CV12 Hop plant.
Figure 4:
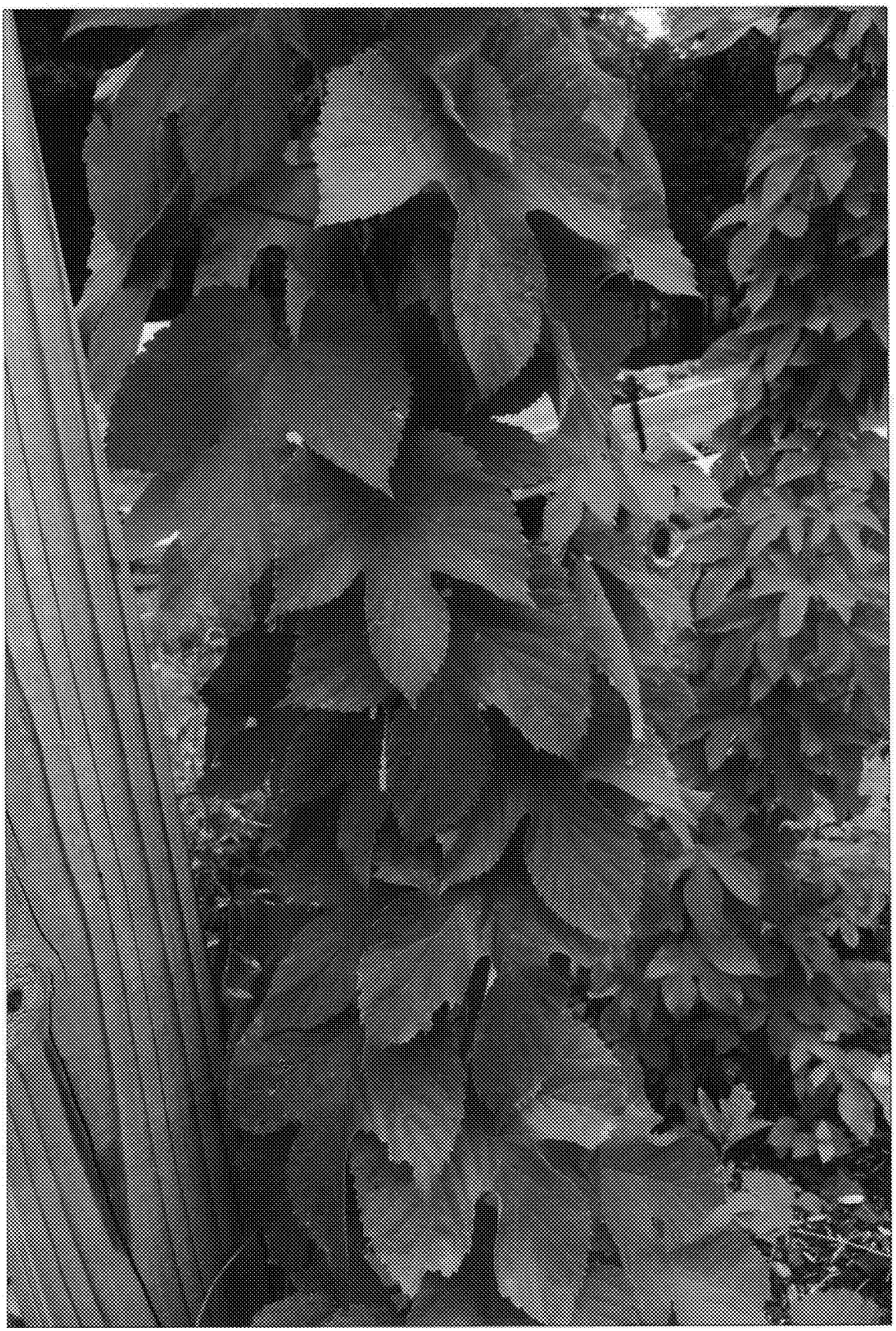
FIG. 4 shows a bine of the CV12 Hop plant before flowering.
Figure 5:
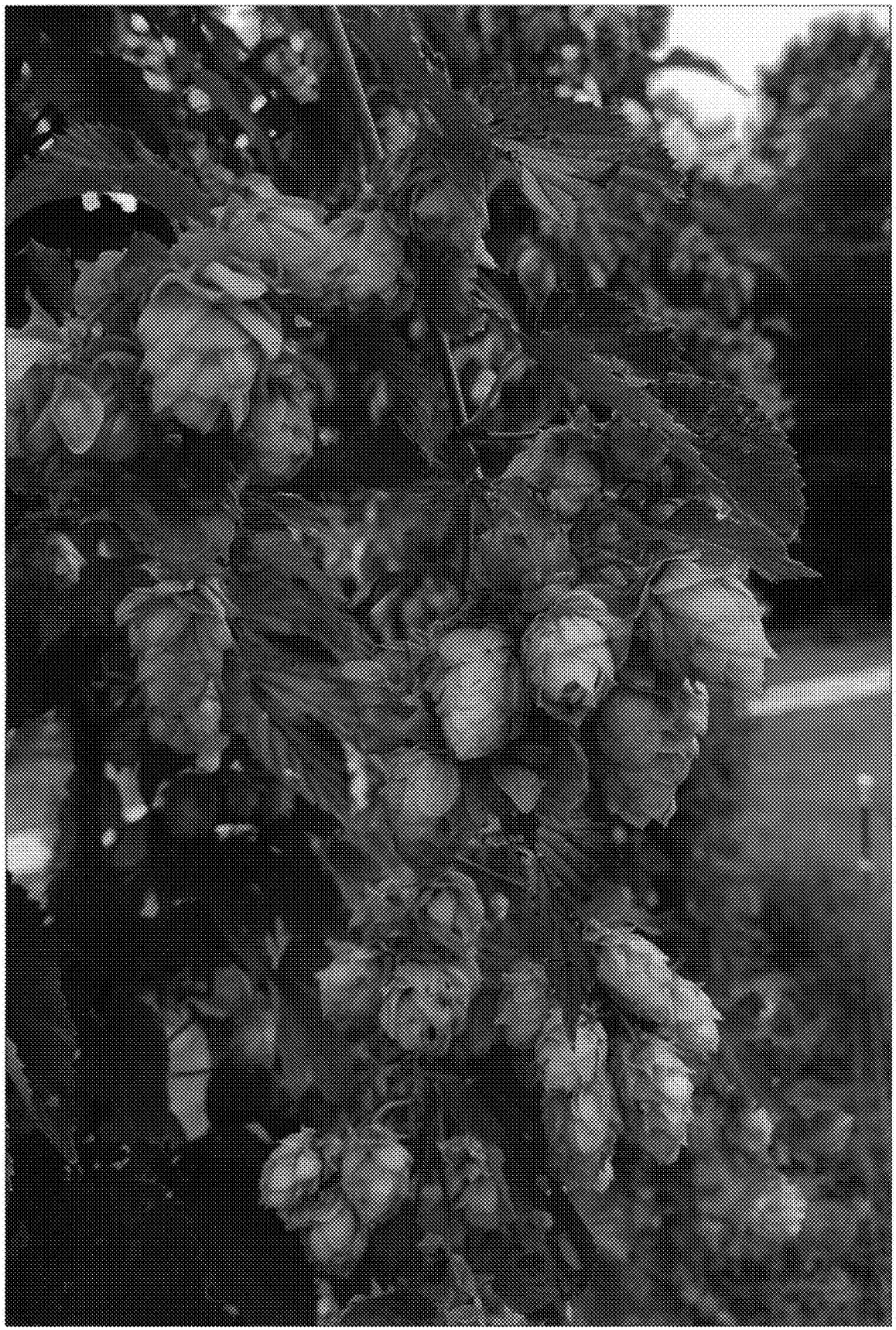
FIG. 5 shows the bine and cones of the CV12 Hop plant prior to picking

The following description is based on observations made during the summer of 2019 growing season at Modesto, Monroe Co. Ind. It should be understood that the characteristics described herein will vary depending upon cultural practices and climatic conditions, as well as with location and season. All colors are described according to The Royal Horticultural Society Colour Chart, Edition V. Quantified measurements are expressed as an average of the measurements taken from a number of individual plants of the new variety. The measurements of any individual plant, or any group of plants of the new variety may vary from the stated average.

Species: *Humulus lupulus*.

Use: Brewing — aroma hop.

Growth rate: Fast, reaching >18' in one growing season.

Regional adaptation: Adapted to U.S. Zones 6 and 6a.

Plant shape: Cylindrical to club-shaped.

Time of flowering: Around July 4$^{th}$.

Time of picking: August 21-September 4.

Relative volume of head: Medium to High.

Length of side shoots from the middle third of the plant: Min=0.34 m, max=0.54 m, mean=0.40 m.

Length of side shoots from the upper third of the plant: Min=0.34 m, max=0.64 m, mean=0.48 m.

Number of cones per node from the middle third of the plant: Min=5, max=12, mean=8.5.

Number of cones per node from the upper third of the plant: Min=5, max=12, mean=8.92.

Total number of cones from the middle third of the plant (per lateral shoot): Min=12, max=50, mean=35.7.

Estimated number of cones in middle third of the plant: 680.

Total number of cones from the upper third of the plant (per lateral shoot): Min=16, max=56, mean=42.2.

Estimated number of cones in the upper third of the plant: 800.

Bine:

*Color.*—143C Yellow Green.
*Stripe.*—Present.
*Stripe color.*—61A Purplish Red.
*Stipule direction.*—Up split.
*Stipule color.*—N144C Yellow Green.
*Bine diameter.*—5.75 mm at 6 feet.
*Main shoot anthocyanin color.*—61A Purplish Red.

Leaf:

*Arrangement.*—Opposite.
*Shape.*—Cordate to palmate.
*Average length of mature leaf.*—145.50 mm.
*Average width of mature leaf.*—113.67 mm.
*Color of mature leaf upper surface.*—152A Light Olive Green.
*Color of mature leaf lower surface.*—152A Light Olive Green.
*Color of immature leaf upper surface.*—144B Yellow Green.
*Color of immature leaf lower surface.*—149A Yellow Green.
*Number of lobes.*—0-7.
*Margin.*—Serrate.
*Serrations per inch.*—5.
*Average petiole length (mature).*—46.00 mm.
*Petiole color at base.*—61A Purplish Red.
*Venation pattern.*—Palmate.
*Vein color.*—128D Pale Green.
*Internode color.*—143C Yellow Green.
*Leaf resin gland color.*—150D Yellow Green.
*Amount of leaf blistering on the upper side of the blade.*—Weak to Absent.

Reproductive organs:

*Bract tip color.*—N 144C Yellow Green.
*Bract tip shape.*—Cuspidate.
*Bract tip position.*—Slightly everted.
*Bract diameter.*—17.08 mm.
*Bract length at apex.*—1-2.5 mm.
*Bract base color.*—N 144C Yellow Green.
*Bracteole diameter.*—18.75 mm.
*Bracteole shape.*—Narrowly ovate.
*Bracteole color.*—144D Yellow Green.
*Compactness.*—Loose.
*Cone shape.*—Ovate.
*Cone length.*—43.40 mm.
*Cone diameter at shoulder.*—22.50 mm.
*Cone tip shape.*—Bluntly Pointed.
*Cone weight.*—1.75 g.
*Cones per node.*—10-12.
*Pickability.*—Good.
*Lupulin gland color.*—14A Yellow.
*Aroma.*—Spicy/Piney/Citrus.

Qualitative analysis:

*Alpha acids (as % of cone weight; method—ASBC hops—6).*—6.4%.
*Beta acids (as % of cone weight; method—ASBC hops—6).*—4.9%.
*Hop storage index (method—ASBC hops—12).*—0.23.

Essential oil profile:

| Retention Time | Component | Percent - % |
|---|---|---|
| 10.045 | 3-Hexanone,4-methyl- | 0.04 |
| 12.282 | Isobutylisobutyrate | 0.34 |
| 12.793 | Methylhexanoate | 0.10 |
| 13.461 | Pinene<alpha> | 0.17 |
| 15.518 | Isoamylpropionate | 0.89 |
| 16.054 | Pinene<beta-> | 1.25 |
| 16.895 | Myrcene | 57.66 |
| 17.105 | Unidentified | 0.05 |
| 18.072 | Isoamylisobutyrate | 0.52 |
| 18.292 | 2-Methylbutylisobutyrate | 2.31 |
| 18.777 | Methylheptanoate | 0.3 |
| 18.973 | Unidentified | 0.37 |
| 19.261 | Limonene | 0.38 |
| 19.375 | Phellandrene<beta> | 0.51 |
| 19.618 | Ocimene<Z-beta> | 0.05 |
| 20.317 | Ocimene<E-beta> | 0.44 |
| 22.981 | Methyl6-methylheptanoate | 0.78 |
| 23.288 | Nonanone<2-> | 0.09 |
| 23.926 | Linalool | 0.37 |
| 24.145 | Methylbutyl-2-methylbutyrate<2-> | 0.06 |
| 24.51 | Methylbutylisovalerate<2-> | 0.11 |
| 25.56 | Methyloctanoate | 1.63 |
| 30.032 | Nonanoicacid,methylester | 0.27 |
| 30.334 | Methyl6-methyloctanoate | 0.14 |
| 31.611 | 4-Nonenoicacid,methylester | 0.11 |
| 32.504 | Methylnonanoate | 0.38 |
| 34.34 | Geraniol | 0.47 |
| 34.773 | Undecanone<4-> | 0.08 |
| 36.092 | Cyclooctylacetate | 0.07 |
| 36.874 | Unidentified | 0.54 |
| 37.263 | Undecanone<2-> | 0.8 |
| 38.289 | Methyldecenoate<4>Z | 2.94 |
| 38.592 | Unidentified | 1.72 |
| 39.152 | Geranate<methyl-> | 0.13 |
| 39.336 | Methyldecanoate | 2.17 |
| 42.837 | Copaene<alpha> | 0.18 |
| 43.512 | Unidentified | 0.54 |
| 43.943 | Dodecanone<2> | 0.11 |
| 45.728 | Caryophyllene<beta> | 5.61 |
| 45.846 | Methylundecanoate | 0.07 |
| 46.311 | Copaene<beta> | 0.13 |
| 48.023 | Humulene<alpha> | 9.89 |
| 48.711 | Undecenylacetate | 0.16 |
| 48.943 | Cadina-1(6),4-diene<cis-> | 0.16 |
| 49.115 | Cadina-1(6),4-diene<trans> | 0.29 |
| 50.022 | Selinene<beta-> | 0.48 |
| 50.31 | Tridecan-2-one | 0.36 |
| 50.465 | Unidentified | 1.43 |
| 50.924 | Methyl3,6-dodecadienoate | 0.24 |
| 51.054 | Geranylisobutyrate | 0.39 |
| 51.171 | Unidentified | 0.19 |
| 51.472 | Amorphene<delta> | 0.40 |
| 51.763 | Cadinene<delta> | 0.63 |
| 52.043 | Zonarene + Methyldodecanoate | 0.19 |
| 52.624 | Cadine-1,4-diene<trans-> | 0.06 |
| 59.907 | Unidentified | 0.2 |

What is claimed is:

1. A new and distinct Hop plant substantially as illustrated and described herein.

* * * * *

A
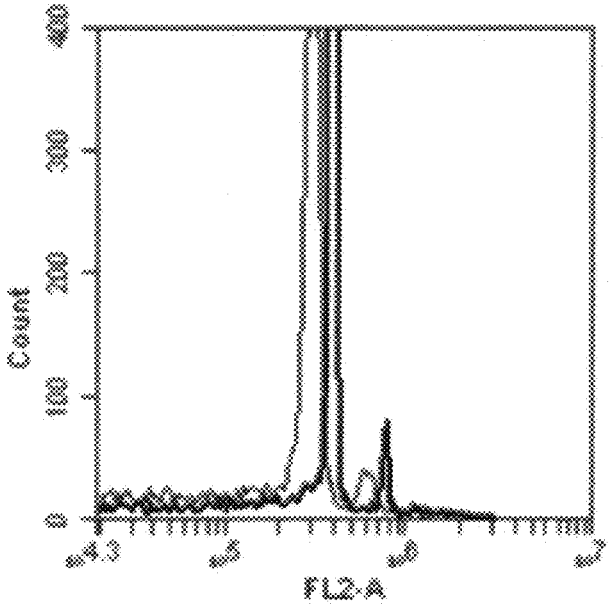
B
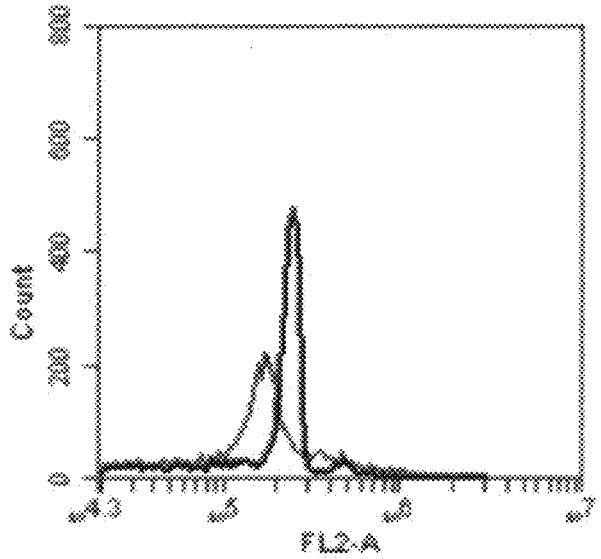
Figure 3 Genome size comparisons of propidium iodide dyed nuclei isolated from young leaves of hops CVC plants (darker line) and hops CV12 plants (lighter line). (A) CV12 leaves taken from clonal generation 3. (B) CV12 leaves taken from clonal generation 4.